United States Patent [19]
Burgess et al.

[11] Patent Number: 5,495,056
[45] Date of Patent: Feb. 27, 1996

[54] PRODUCTION OF HYDROFLUOROCARBONS

[75] Inventors: Leslie Burgess; Thomas A. Ryan; Richard L. Powell, all of Cheshire, United Kingdom

[73] Assignee: Imperial Chemical Industries PLC, London, England

[21] Appl. No.: 355,306

[22] Filed: Dec. 12, 1994

Related U.S. Application Data

[63] Continuation of Ser. No. 76,123, Jun. 14, 1993, abandoned.

[30] Foreign Application Priority Data

Jun. 18, 1992 [GB] United Kingdom ............... 9212925

[51] Int. Cl.$^6$ .................................................. C07C 19/08
[52] U.S. Cl. .................................................. 570/142
[58] Field of Search ...................................... 570/142

[56] References Cited

U.S. PATENT DOCUMENTS 4,357,282  11/1982  Anderson et al. .

FOREIGN PATENT DOCUMENTS 518506  12/1992  European Pat. Off. .
0070625  4/1984  Japan ................................. 570/142

OTHER PUBLICATIONS

Knunyants et al., Some Reactions of Fluorine–Containing Ethers, Bulletin of the Academy of Sciences of the USSR Division of Chemical Science, vol. 21, No. 10, Oct. 1972 pp. 2177–2180.

George Van Dyke Tiers, The Chemistry of Perfluoro Ethers. II. Ether Cleavage with Simultaneous Replacement of $\alpha$–Fluorine by Chlorine, Journal of the American Chemical Society, vol. 77, 20 Dec. 1955, pp. 6703–6704.

Hudlicky, "Reaction of Alkyl 2–Chloro–1,1, 2–Trifluoroethyl Ethers with Lewis Acids", Journal of Fluorine Chemistry, 29 (1985) pp. 349–354.

England, "Catalytic Conversion of Fluoroalkyl Alkyl Ethers to Carbonyl Compounds", J. Org. Chem. 1984, 49, pp. 4007–4008.

*Primary Examiner*—Alan Siegel
*Attorney, Agent, or Firm*—Cushman Darby & Cushman

[57] ABSTRACT

A process for the production of hydrofluorocarbons, in particular hydrofluoroalkanes such as difluoromethane, which comprises contacting an $\alpha$-fluoro-ether, in particular a fluorinated dialkyl ether such as bis(fluoromethyl)ether in the liquid phase with a Lewis acid such as a fluoride of Nb, Sb, B, Ta, Al or Ti.

8 Claims, No Drawings

PRODUCTION OF HYDROFLUOROCARBONS

This is a continuation of Application No. 08/076,123, filed on Jun. 14, 1993, now abandoned, which was abandoned upon the filing hereof.

This invention relates to a process for the production of hydrofluorocarbons and more particularly to a process for the production of hydrofluoroalkanes.

In recent years chlorofluorocarbons, which are used on a large scale around the world, have been perceived as having an adverse effect on the ozone layer and/or as contributing to global warming. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned environmentally harmful effects. One approach in the search for suitable replacements has centred on fluorocarbons which do not contain chlorine but which may contain hydrogen, that is hydrofluorocarbons, of which many have been proposed as suitable replacements.

Several methods for the preparation of hydrofluorocarbons are known but many of these methods involve the use of chlorine-containing starting materials and the production of chlorine-containing by-products.

In our co-pending UK Patent Application No. 9126355.8 there is described a chlorine-free process for the production of hydrofluorocarbons which comprises heating an α-fluoroether to elevated temperature in the vapour phase.

We have now found that α-fluoroethers may also be caused to decompose in the liquid phase to yield hydrofluorocarbons.

According to the present invention there is provided a process for the production of a hydrofluorocarbon which comprises contacting an α-fluoro-ether in the liquid phase with a Lewis acid.

The process of the present invention is especially useful in the production of hydrofluoroalkanes and according to a further aspect of the invention there is provided a process of producing a hydrofluoroalkane having the formula $C_nH_xF_y$ in which n is an integer from 1 to 6, y is an integer of at least 2 and $x=2n+2-y$, which comprises contacting an α-fluoroether in the liquid phase with a Lewis acid.

In the hydrofluoroalkane of formula $C_nH_xF_y$, n is preferably an integer from 1 to 4 and y is preferably an integer from 2 to 9; more preferably n is 1 or 2, and y is an integer from 2 to 5. Where n is 1, y is especially preferably 2, and the hydrofluoroalkane product of the invention may be difluoromethane, di-, tri-, tetra- or penta-, fluoroethane. We especially prefer to employ the process of the invention as a process of producing difluoromethane, 1,1,1,2-tetrafluoroethane and pentafluoroethane.

By an α-fluoro-ether there is meant an ether having a fluorine atom attached to a carbon atom at the α-position relative to the oxygen atom, that is an ether containing the group —C—O—CF—. A particularly useful class of ethers is that having the general formula R—O—CF—$R^1R^2$, wherein R, $R^1$ and $R^2$ are as hereinafter defined.

We have found that these α-fluoro-ethers of formula R—O—CF—$R^1R^2$ may be caused to breakdown in the liquid phase upon contact with a Lewis acid to yield hydrofluorocarbons R—F.

In the ethers of formula R—O—CF—$R^1R^2$, the group R may generally take any form and may comprise heteroatoms, for example O, S or N, provided that it comprises at least one carbon atom. The group R may be for example saturated or unsaturated, linear or branched chain, cyclic or acyclic, aliphatic or aromatic.

However, the process of the present invention is, as previously stated, useful in particular for the production of hydrofluoroalkanes from the class of ethers in which the R group is an optionally substituted alkyl group which may comprise one, two or even more carbon atoms, say up to 6 or even more carbon atoms. The alkyl group R will usually be a straight chain alkyl group although it may also be a branched chain alkyl group. The group R may comprise only carbon and hydrogen although usually the group R will be a fluorinated group.

The α-fluoro ether will typically be an α-fluoroalkyl ether, that is an ether of formula R—O—CF—$R^1R^2$ wherein $R^1$ and $R^2$ are hydrogen, fluorine or optionally substituted alkyl groups which may comprise one, two or even more carbon atoms, say up to 6 or even more carbon atoms. The alkyl groups $R^1$ and $R^2$ will usually be acyclic straight chain alkyl groups although they may also be acyclic branched chain alkyl groups or cyclic alkyl groups. The groups $R^1$ and $R^2$ may comprise only carbon and hydrogen although usually the groups $R^1$ and $R^2$ will be fluorinated groups. Typically at least one of $R^1$ and $R^2$ will be a hydrogen atom. Preferably neither of $R^1$ and $R^2$ will be a fluorine atom.

Thus, according to a preferred embodiment of the invention there is provided a process for the production of hydrofluoroalkanes which comprises contacting an α-fluoroether having the formula R—O—CF—$R^1R^2$ wherein R is an optionally substituted alkyl group comprising from 1 to 6 carbon atoms and $R^1$ and $R^2$ are H, F or optionally substituted alkyl groups containing from 1 to 6 carbon atoms, in the liquid phase with a Lewis acid. Preferably the group R also contains at least one fluorine atom; and $R^1$ and $R^2$ are not F.

The α-fluoro-ether is preferably an α-fluoromethyl-ether, R—O—$CFH_2$, or a tetrafluoroethyl ether R—O—CFH—$CF_3$, since these α-fluoro-ethers are readily prepared and on contact in the liquid phase with a Lewis acid yield particularly useful hydrofluoroalkanes.

The α-fluoromethyl-ether may be, for example, $FCH_2$—O—$CH_2F$ bis(fluoromethyl)ether, $FCH_2$—O—$CH_3$ fluoromethyl-methyl ether, $FCH_2$—O—$CH_2CF_2H$ 1,1,-difluoroethyl-fluoromethyl ether; or $FCH_2$—O—$CH_2CF_3$ 1,1,1-trifluoroethyl-fluoromethyl ether, which when contacted in the liquid phase with a Lewis acid may decompose to yield the following hydrofluoroalkanes respectively, $CH_2F_2$, $CH_3F$, $CHF_2CH_2F$ and $CF_3CH_2F$. The tetrafluoroethyl ether may be, for example, $CF_3CHF$—O—$CH_2CF_3$, which upon contact in the liquid phase with a Lewis acid may yield 1,1,1,2-tetrafluoroethane, or $CF_3CFH$—O—$CFHCF_3$ or $CF_3CHF$—O—$CH_2F$ which upon contact in the liquid phase with a Lewis acid may yield $CF_3CF_2H$.

According to a first preferred embodiment of the invention there is provided a process for the production of 1,1,1,2-tetrafluoroethane comprising contacting $CF_3CHX$—O—$CFR^1R^2$ in which X is H or F and $R^1$ and $R^2$ are H, F or an optionally substituted alkyl group containing from 1 to 6 carbon atoms, in the liquid phase with a Lewis acid. The ether is preferably $FCH_2$—O—$CH_2CF_3$ and/or $CF_3CHF$—O—$CH_2CF_3$.

According to a second preferred embodiment of the invention there is provided a process for the production of pentafluoroethane comprising contacting $CF_3CHF$—O—$CFR^1R^2$ in which $R^1$ and $R^2$ are as defined in the previous paragraph, in the liquid phase with a Lewis acid. The ether is preferably $CF_3CFH$—O—$CFHCF_3$ and/or $CF_3CFH$—O—$CH_2F$.

According to a third preferred embodiment of the invention there is provided a process for the production of difluoromethane comprising contacting an α-fluoroether having the formula $CH_2F$—O—$CFR^1R^2$ in which $R^1$ and $R^2$ are as defined in the first preferred embodiment of the invention, in the the liquid phase with a Lewis acid. The ether is preferably bis(fluoromethyl)ether.

The term "Lewis acid" is commonly known and used by those skilled in the art, and any Lewis acid, for example $AlCl_3$, may be employed in the process of the invention. We have found that materials which are not Lewis acids, for example, the Bronsted acids such as nitric, trifluoroacetic, sulphuric, fluorosulfonic and trifluoromethane sulphonic acids; and other materials such as KF, $MnF_3$ and glass are not effective in the production of hydrofluorocarbons from α-fluoroethers. Furthermore, materials which are known to be effective for the liquid phase decomposition of alkyl fluoroformates, for example quaternary ammonium salts such as tetrabutyl ammonium fluoride, have no utility in the liquid phase α-fluoroether decomposition process of the present invention.

Particularly suitable Lewis acids for use in the process of the invention contain fluoride as the anionic species, since where anionic species other than fluoride are present, in particular halides other than fluoride, e.g. chlorides, many undesirable by-products may be produced. However anionic species other than fluoride, for example halide other than fluoride, alkoxide, etc, do result in the production of hydrofluorocarbons and may be employed if desired. Preferred Lewis acids include the fluorides of elements, in particular metals, of Group III (a or b), IV (a or b) and V (a or b) of The Periodic Table of the Elements, for example $AlF_3$, $BF_3$, $SnF_4$, $TaF_5$, $TiF_4$, $NbF_5$ and $SbF_5$.

We particularly prefer to employ Lewis acids in which the central cation, usually a metal, has a charge/radius ratio of at least 5.0 and preferably at least 6.0. We especially prefer to employ $SbF_5$, $BF_3$, $NbF_5$ and/or $TiF_4$ in the process of the invention. Mixtures of Lewis acids may be employed, if desired.

The Lewis acid may be generated in situ, for example by employing the corresponding halides other then fluorides, for example chlorides, or oxides and a source of fluoride, for example hydrogen fluoride. They may also be generated in situ by employing the metal itself and a source of fluoride, especially hydrogen fluoride.

The process may be conducted in the presence or absence of hydrogen fluoride. We prefer to conduct the process in the presence of hydrogen fluoride. The amount of hydrogen fluoride employed may vary within a wide range but generally a stoichiometric excess of hydrogen fluoride to bis(fluoromethyl)ether is preferred. The molar ratio of bis(fluoromethyl)ether to hydrogen fluoride may be in the range from about 2:1 to about 1:50, preferably in the range from about 1:2 to about 1:20. The hydrogen fluoride may serve not only to improve the conversion of the ether and the selectivity to difluoromethane but also to regenerate the Lewis acid thereby rendering the process of the invention catalytic.

The process is preferably conducted under substantially anhydrous conditions, since many of the Lewis acids are readily hydrolysed. However, the susceptibility of any particular Lewis acid to hydrolysis by water varies with the particular Lewis acid employed and it is not essential that the process is conducted under substantially anhydrous conditions; indeed certain Lewis acids may be employed in the form of their hydrates, for example $BF_3$.

The process is carried out under conditions of temperature and pressure such that the α-fluoroether is in the liquid phase. Preferred conditions of temperature and pressure are such that the α-fluoroether is in the liquid phase and the hydrofluorocarbon product is in the vapour phase, as the hydrofluorocarbon product of the process may then easily separate from the reaction mixture. However the hydrofluorocarbon product may also be liquid under the conditions of the process, if desired. Thus, the particular conditions of temperature and pressure employed will be dependent to some extent upon the particular ether employed. Generally, the temperature will be in the range from about −50° C. to about 300° C. depending to some extent upon the pressure employed and preferably in the range from about −30° C. to about 200° C., more preferably from about −20° C. to about 150° C. Where atmospheric pressure operation is employed the temperature will usually be in the range from about −20° C. to about 100° C. Atmospheric pressures are conveniently employed although superatmospheric pressure or subatmospheric pressure may be employed if desired.

Processes are known for the production of at least some specific α-fluoro-ethers and any of these known processes may be used for the production of the α-fluoro-ether starting materials in the present invention. Thus, for example, the α-fluoro-ether may be produced as described in The Journal of Inorganic Nuclear Chemistry-32, (1970), 1748, The Journal of the American Chemical Society 82 (1960) 543, or The Journal of Organic Chemistry, 28, 492 (1963).

However, we have found that a particularly convenient, and thus preferred, general method for the production of the α-fluoro-ether is by reacting a non-enolisable aldehyde with hydrogen fluoride, preferably in the liquid phase, and in the presence of an alcohol.

According to a preferred embodiment of the invention there is provided a process for the production of a hydrofluorocarbon which comprises (a) contacting a non-enolisable aldehyde with hydrogen fluoride in the liquid phase in the presence of an alcohol to produce an α-fluoro-ether and (b) contacting the α-fluoro-ether in the liquid phase with a Lewis acid.

A non-enolisable aldehyde is required in order that the aldehyde is not polymerised in hydrogen fluoride when the two are reacted together.

The non-enolisable aldehyde employed is preferably formaldehyde or trifluoroacetaldehyde since these aldehydes are the most readily available non-enolisable aldehydes and they yield the most useful final hydrofluorocarbons: formaldehyde is particularly preferred. Indeed, in a further preferred embodiment of the invention, both formaldehyde and trifluoroacetaldehyde are reacted with hydrogen fluoride to produce a mixture of $CF_3CFH$—O—$CH_2F$ and $CH_2F$—O—$CH_2F$. This mixture may then be converted to hydrofluoroalkanes, or a separate alcohol may then be added to this mixture to produce further α-fluoroethers.

Production of the α-fluoroether may be conveniently effected simply by dissolving the non-enolisable aldehyde in any of its readily available forms in liquid hydrogen fluoride at about room temperature, in the presence of an alcohol.

The non-enolisable aldehyde may be provided in any of its known forms. Thus formaldehyde may be provided, for example, in one of its polymeric forms, paraformaldehyde or trioxane, or in its monomeric form which may be provided, for example, from a process stream in which it has been freshly made, for example by the oxidation of methanol. Trifluoroacetaldehyde may be provided, for example, in its hydrated form $CF_3CH(OH)_2$ or in its dehydrated form $CF_3CHO$.

Accordingly, whenever used herein, the term non-enolisable aldehyde is to be understood as including non-enolisable aldehydes in any of their known forms.

In general, where formaldehyde is used as the non-enolisable aldehyde, a polymeric form of formaldehyde such as paraformaldehyde is preferred where the formaldehyde is dissolved in liquid hydrogen fluoride. Paraformaldehyde and trioxane dissolve readily in liquid hydrogen fluoride and the production of the α-fluoro-ether may be conveniently carried out by dissolving paraformaldehyde or trioxane in liquid hydrogen fluoride at about room temperature and at about atmospheric pressure in the presence of an alcohol.

The molar ratio of the non-enolisable aldehyde to hydrogen fluoride may vary considerably, for example in the range about 1:0.5 to 1:50 but in general a stoichiometric excess of hydrogen fluoride is preferred. Typically, the molar ratio of non-enolisable aldehyde to hydrogen fluoride will be in the range about 1:2 to about 1:10.

The reaction of the non-enolisable aldehyde with hydrogen fluoride is carried out in the presence of an alcohol. The alcohol may be generated in situ. Thus, the reaction of the non-enolisable aldehyde, for example formaldehyde or trifluoroacetaldehyde, with hydrogen fluoride is believed to yield an intermediate alcohol $FCH_2OH$ and $CF_3CHFOH$ respectively which may then condense to give the α-fluoro-ether $FCH_2$—O—$CH_2F$ and $CF_3CFH$—O—$CFHCF_3$ respectively.

Alternatively a wider range of α-fluoro-ethers may be produced by adding a separate alcohol. Where a separate alcohol is added, it may be added at the same time as the hydrogen fluoride and non-enolisable aldehyde, or it may be added subsequently to the mixture of aldehyde and hydrogen fluoride. Furthermore the alcohol may be first added to the hydrogen fluoride and the aldehyde may then be added to this reaction mixture. Thus the order of addition of the hydrogen fluoride, aldehyde and alcohol is not critical.

Where the alcohol is added separately, the alcohol may have the general formula R—OH provided that the alcohol must be inert to hydrogen fluoride and the α-fluoro-ether. The group R may become the R group of the ether produced having the general formula R—O—CF—$R^1R^2$. The groups R, $R^1$ and $R^2$ are as hereinbefore defined.

Whilst production of the α-fluoroether is not limited by theory and the following theory is given merely by way of explanation, the provision of a separate alcohol effectively leads to a transetherification with the ether produced by condensation of two molecules of the alcohol believed to be generated in situ by the reaction of hydrogen fluoride with the non-enolisable aldehyde. Thus, as previously described where a separate alcohol is not added to hydrogen fluoride and formaldehyde, two molecules of the transient intermediate $FCH_2OH$ condense to give $CH_2F$—O—$CH_2F$. Where a separate alcohol is present one of the —$CH_2F$ groups is effectively substituted by the group R of the separate alcohol which is present. This may occur by way of transetherification of the alcohol R—OH with $CH_2F$—O—$CH_2F$, or by condensation of $FCH_2OH$ with R—OH. However, the precise mechanism is not important as the effective final ether produced is the same.

The group R may generally take any form provided that it comprises at least one carbon atom, and the group R may for example be saturated or unsaturated, linear or branched chain, cyclic or acyclic, aliphatic or aromatic. The group R may also comprise heteroatoms, for example O, S or N.

However, the process of this further preferred embodiment of the present invention is useful in particular for the production of ethers in which the R group is an optionally substituted alkyl group which may comprises one, two or even more carbon atoms, say up to 6 or even more carbon atoms. The alkyl group R will usually be a straight chain alkyl group although it may also be a branched chain alkyl group. The R group may comprise only hydrogen and carbon, for example the R group may be $CH_3$, $C_2H5$. Preferably however, the R group will be fluorinated, for example the R group may be $FCH_2CH_2$—, $HCF_2CH_2$—, $CF_3CH_2$—, $(CF_3)_2CH$—, or $CF_2HCF_2CH_2$—. Thus the alcohol which is added is preferably a primary alcohol and may comprise such R groups, for example the alcohol may be methanol, ethanol, 2-monofluoroethanol, 2,2-difluoroethanol, 2,2,2-trifluoroethanol, hexafluoroisopropanol or 1,1,2,2-tetrafluoropropanol. Some at least of the alcohols may be generated in situ by adding an epoxide to the non-enolisable aldehyde/hydrogen fluoride mixture. Thus for example, 2-monofluoroethanol may be generated in situ by the addition of ethylene glycol which reacts with hydrogen fluoride to produce 2-monofluoroethanol.

Where the alcohol is added separately, it may be added in similar proportions as the non-enolisable aldehyde, that is, in the molar ratio of alcohol to hydrogen fluoride for example in the range about 1:0.5 to 1:50 but in general a stoichiometric excess of hydrogen fluoride is preferred. The proportion of alcohol added may also depend upon the particular alcohol used since we have found that with certain alcohols, the addition of too great a proportion of the alcohol leads to the formation of an undesirable acetal rather than the required α-fluoroether. Typically the molar ratio of alcohol to hydrogen fluoride will be in the range about 1:2 to about 1:10.

The α-fluoro-ether may be isolated from the aldehyde and hydrogen fluoride, from which it is produced, and any by-products, before the α-fluoro-ether is contacted in the liquid phase with a Lewis acid. The ether may be isolated, for example, by adding alkali to the non-enolisable aldehyde/hydrogen fluoride/alcohol liquid mixture and heating the resulting alkaline solution, for example up to about 50° C., in order to drive the α-fluoro-ether off. Alternatively the α-fluoroether may conveniently be isolated by contacting the product stream with water at a temperature in the range from about 50° C. to about 80° C. The α-fluoro ether may then be collected in a cold trap or passed directly to the heating zone.

We especially prefer that the α-fluoroether and optionally hydrogen fluoride are separated from water which is also produced by the reaction of the non-enolisable aldehyde with hydrogen fluoride. Thus the α-fluoroether and optionally hydrogen fluoride are preferably contacted in the liquid phase with a Lewis acid in the substantial absence of water. Preferably the α-fluoroether and optionally hydrogen fluoride which is contacted with the Lewis acid contains less than 5% by weight water, more preferably less than 1% by weight and especially less than 0.5% by weight water, although the use of certain Lewis acids, in particular $BF_3$, may allow the process of the invention to be performed without a loss in selectivity to the desired product in the presence of lager quantities of water.

In particular, we have achieved high conversions of bis(fluoromethyl)ether and high selectivities to difluoromethane with many Lewis acids where the bis(fluoromethyl)ether/hydrogen fluoride mixture which is contacted with the Lewis acid contains from about 500 ppm to about 3000 ppm of water.

Separation of the α-fluoroether and optionally hydrogen fluoride from water may be achieved in any suitable manner, and conveniently for example by vaporising the α-fluoroether and optionally hydrogen fluoride from the product mixture obtained by reacting a non-enolisable aldehyde with hydrogen fluoride in the presence of an alcohol, or by contacting the product mixture with a solid drying agent. Thus, for example a stream of an inert gas, for example nitrogen may be sparged through the solution of α-fluoroether and hydrogen fluoride (and other by-products).

Accordingly, in a further embodiment of the invention there is provided a process for the production of a hydrofluoroalkane which comprises the steps of (a) reacting a non-enolisable aldehyde with liquid hydrogen fluoride in the presence of an alcohol to produce an α-fluoroether, (b) separating at least some water from the product of step (a) and (c) contacting the α-fluoro-ether and optionally hydrogen fluoride in the liquid phase with a Lewis acid.

The production of the especially preferred α-fluoroether, bis(fluoromethyl)ether for use in the process of the present invention is described in our published European Patent Application No. 0 518 506, the contents of which are incorporated herein by reference in so far as they relate to the production of bis(fluoromethyl)ether.

The invention is illustrated, but not limited, by the following examples.

EXAMPLE 1

3.2 g of bis(fluoromethyl)ether were charged to a 30 ml FEP (copolymer of hexafluoropropylene and tetrafluoroethylene) bottle, a septum cap was fitted and the bottle was cooled in ice to 0° C. 0.3 g of $SbF_5$ were injected into the bottle, the bottle was shaken and the head space above the liquid was analysed by gas chromatography, mass spectrometry and infra-red spectroscopy. The results, based on integration of the peaks in the gas chromatograph are shown below:

| HEAD SPACE PRODUCT | % (v/v) |
| --- | --- |
| $CH_2F_2$ | 8.16 |
| $CH_2O$ | 0.16 |
| $CH_2F-O-CH_2F$ | 91.6 |
| Others | 0.08 |

EXAMPLE 2

The procedure of example 1 was repeated except that 0.5 g of aluminium chloride was added to 2.0 g of bis(fluoromethyl)ether. The results of analysis of a sample taken from the head space, based on gas chromatagram peak areas, are given below.

| HEAD SPACE PRODUCT | % (v/v) |
| --- | --- |
| $CH_2F_2$ | 0.05 |
| $CH_3-O-CH_2F$ | 0.02 |
| $CH_2F-O-CH_2F$ | 97.6 |
| $CH_2F-O-CH_2Cl$ | 2.2 |
| $CH_2F-O-CH_2-O-CH_2F$ | 0.13 |

0.2 mls of anhydrous hydrogen fluoride were then added to the mixture in the FEP bottle and the headspace was reanalysed. The results are shown below:

| HEAD SPACE PRODUCT | % (v/v) |
| --- | --- |
| $CH_3F$ | 0.01 |
| $CH_2F_2$ | 0.2 |
| $CH_3-O-CH_2F$ | 0.06 |
| $CH_2F-O-CH_2F$ | 87.0 |
| $CH_2F-O-CH_2Cl$ | 12.53 |
| $CH_2F-O-CH_2-O-CH_2F$ | 0.1 |
| $CH_2Cl_2$ | 0.1 |

The following examples 3 to 23 were conducted in a 125 ml Hastelloy 'C' autoclave.

EXAMPLE 3

21.0 g of bis(fluoromethyl)ether (containing about 1000 ppm of water) and 0.7 g of $NbF_5$ were charged to the autoclave and the autoclave was heated to a maximum of 186° C. over a period of 3 hours. After this time the volatile organic products were separated from the catalyst/residues by distillation and the organics were analysed by Gas Chromatograhy, Infra-red spectroscopy and Mass Spectrometry. The results are shown below:

| Product | Yield (%) |
| --- | --- |
| Difluoromethane | 10.8 |
| Methyl fluoride | 34.1 |

EXAMPLE 4

The procedure of example 3 was repeated except that the maximum temperature was 84° C. The results are shown below:

| Product | Yield (%) |
| --- | --- |
| Difluoromethane | 2.9 |
| Methyl fluoride | 9.4 |

EXAMPLES 5 to 13

The procedure of example 3 was repeated with the Lewis acids stated in Table 1. The presence and amount thereof of hydrogen fluoride; the catalyst employed and the maximum temperature are given in Table 1.

TABLE 1

| Lewis acid. | HF | BFME | Max Temp. | Yield (%). | |
| --- | --- | --- | --- | --- | --- |
| (g) | (g) | (g) | (°C.) | $CH_2F_2$ | $CH_3F$ |
| $SbF_5$ 4.2 | 52.3 | 41.0 | 101 | 45.8 | 7.5 |
| $TiF_4$ | 25.7 | 20.6 | 141 | 46.2 | 49.4 |

TABLE 1-continued

| Lewis acid. (g) | HF (g) | BFME (g) | Max Temp. (°C.) | Yield (%). | |
|---|---|---|---|---|---|
| | | | | $CH_2F_2$ | $CH_3F$ |
| 7.0 $AlF_3$ | 26.2 | 20.6 | 162 | 4.67 | 58.3 |
| 5.0 $TaF_5$ | 23.4 | 20.5 | 130 | 60.5 | 35.9 |
| 7.0 $NbF_5$ | 25.3 | 20.5 | 125 | 55.0 | 25.6 |
| 7.0 $NbF_5$ | 23.5 | 20.5 | 50 | 61.8 | 14.0 |
| 5.0 CsF | 24.5 | 20.0 | 161 | 9.4 | 0.8 |
| 7.0 $BF_3$ | 32.2 | 18.1 | 65 | 46.6 | 18.3 |
| 1.6 $BF_3.2H_2O$ | 361.5 | 361.5 | 50 | 10.2 | 84.2 |
| 96 | | | | | |

EXAMPLE 14

The procedure of example 3 was repeated except that 18 g of fluoromethyl-2,2,2-trifluoroethyl ether, 27.5 g of hydrogen fluoride and 5 g of $TaF_5$ were heated to a maximum of 178° C. The results are shown below:

| Product. | Yield (%). |
|---|---|
| Difluoromethane | 40.0% |
| 1,1,1,2-tetrafluoroethane | 5.0% |

COMPARATIVE EXAMPLES 1 to 3

The procedure of example 3 was repeated except that a Lewis acid was not present. The amounts of BFME and HF present are given in Table 2 below. In comparative example 3 various materials which were not Lewis acids were employed, as stated.

TABLE 2

| HF (g) | BFME (g) | Other (g) | Max Temp. (°C.) | Yield (%). | |
|---|---|---|---|---|---|
| | | | | $CH_2F_2$ | $CH_3F$ |
| 0.0 | 26.0 | None | 200 | 0.2 | 0.1 |
| 25.4 | 20.5 | None | 155 | 6.8 | 72.1 |
| 24.5 | 20.0 | (a) $MnF_3$ (b) Glass (c) KF (d) $Bu_4NF$ | } Qualitative: No hydrofluorocarbon product | | |

EXAMPLE 15

(a) Preparation of Fluoromethyl-2,2,3,3-tetrafluoropropyl ether.

400 g of anhydrous hydrogen fluoride were added to 80 g of trioxane at 0° C. and to this mixture 160 g of tetrafluoropropanol were added with cooling. The resulting mixture was poured onto ice and the lower organic layer was separated from the aqueous layer. The organic layer collected was dried and purified by vacuum distillation to give an organic fraction having the following composition:

| Component | (%) |
|---|---|
| Fluoromethyl-2,2-3,3-tetrafluoropropyl ether $CHF_2CF_2CH_2—O—CH_2—O—CH_2F$ | 87.0 11.25 |
| Bis(fluoromethyl)ether | 1.75 |

(b) Preparation of 1,1,2,2,3-pentafluoropropane 19.2 g of the composition prepared in (a) was charged to a Hastelloy autoclave together with 17.8 g of anhydrous hydrogen fluoride and 2 g of $NbF_5$. The mixture was heated to a maximum of 85° C. for 16 hours. The volatile organic products were distilled from the autoclave and were analysed b$_7$ gas chromatography and mass spectrometry. The composition of the volatile organic fraction collected is given below:

| Component. | (%) |
|---|---|
| Fluoromethyl-2,2-3,3-tetrafluoropropyl ether | 69.3 |
| 1,1,2,2,3-pentafluoropropane | 23.7 |
| Difluoromethane | 4.3 |
| Methyl fluoride. | 2.7 |

EXAMPLE 16

(a) Preparation of fluoromethyl-2,2,2-trifluoroethyl ether.

20 g of trioxane was added to 100 g of anhydrous hydrogen fluoride with stirring and cooling and to the mixture was added 50 g of 2,2,2-trifluoroethanol at 0° C. The resulting mixture was poured onto iced water. The lower organic layer was separated from the aqueous layer and the organic layer was analysed by Gas chromatography, Infrared spectroscopy and Mass spectrometry. The organic layer had the following composition:

| Component | (%) |
|---|---|
| fluoromethyl-2,2,2-trifluoroethyl ether | 91.6 |
| Bis(fluoromethyl)ether | 5.6 |
| $CF_3CH_2—O—CH_2—O—CH_2F$ | 2.8 |

(b) Preparation of Difluoromethane and 1,1,1,2-tetrafluoroethane.

18.9 g of the composition from (a) was charged to a Hastalloy autoclave together with 19 g of anhydrous hydrogen fluoride and 2 g of $NbF_5$ and the mixture was heated to 100° C. for 2 hours. The volatile organics were distilled from the autoclave and analysed by Mass spectrometry. The composition of the organics collected was as follows:

| Component | (%) |
|---|---|
| fluoramethyl-2,2,2-trifluoroethyl ether. | 29.0 |
| $CF_3CH_2—O—CH_2—O—CH_2F$ | 27.6 |
| $CF_3CH_2—O—CH_2—O—CH_2F$ | 13.6 |
| $CF_3CH_2—O—CH_3$ | 11.7 |
| Difluoromethane | 7.5 |
| Methyl fluoride | 5.9 |
| Bis(fluoromethyl)ether | 2.7 |
| 1,1,1,2-tetrafluoroethane | 2.0 |

EXAMPLE 17

43.7 g of fluoromethyl-2,2,2-3,3,3-hexafluoroisopropylether, 28.7 g of hydrogen fluoride and 2.8 g of $NbF_5$ were charged to a Hastelloy autoclave and heated to a maximum of 50° C. for 16 hours. The volatile organic products were distilled from the autoclave and analysed by Gas chromatography. The composition of the organics collected was as follows:

| Component | (%) |
| --- | --- |
| Difluoromethane | 60.0 |
| Fluoromethyl-2,2,2-3,3,3-hexafluoroisopropylether | 34.0 |
| 1,2,2,2,3,3,3-heptafluoroisopropane | 0.1 |
| Others | 5.9 |

EXAMPLES 18 to 23

In the following examples the procedure of example 3 was followed except that the Lewis acid was generated in situ from the metal or oxide thereof as stated in Table 3 and the amounts of bis(fluoromethyl)ether, hydrogen fluoride and catalyst charged to the autoclave were 20 g, 25 g and 2 g respectively. The results and conditions are shown in Table 3.

TABLE 3

| Metal (or oxide) | Form | Max Temp (°C.) | Conversion $CH_2F$—O—$CH_2F$ (%) | Selectivity $CH_2F_2$ (%) | Selectivity $CH_3F$ (%) |
| --- | --- | --- | --- | --- | --- |
| Hastelloy | Vessel | 155 | 35.5 | 5.4 | 29.9 |
| Antimony | Shot | 100 | 68.2 | 18.4 | 64.3 |
| Niobium | Turnings | 100 | 76.9 | 37.7 | 47.5 |
| Tantalum | Wire | 100 | 99.6 | 20.8 | 77.1 |
| Tungsten | Wire | 100 | 92.5 | 14.4 | 83.5 |
| $Fe_2O_3$ | Powder | 125 | 89.9 | 8.2 | 89.6 |

EXAMPLE 24

600 g of a 50/50% w/w mixture of bis(fluoromethyl)ether and hydrogen fluoride containing 3000 ppm (by weight) water was charged to a 1 litre Hastelloy autoclave at room temperature (19° C.). $BF_3$ was then charged to the closed autoclave to a pressure of 5 barg (approx 10.6 g $BF_3$). The pressure dropped to 4.2 barg as $BF_3$ was absorbed into the liquid, the pot was heated to 50° C. and the pressure rose to 6.6 barg. Five vapour samples were taken from the autoclave headspace at regular intervals over a period of 6 hours whilst the temperature was maintained at 50° C. After each vapour sample was taken, $BF_3$ was charged to the autoclave to maintain the pressure at about 7 barg (approx. 1–2 g $BF_3$). The vapour samples were analysed by gas chromatography. Over the 6 hour period the vapour was found to comprise 94.7% by volume difluoromethane and 4.6% methyl fluoride.

We claim:

1. A process for the production of difluoromethane which comprises contacting the compound $CH_2F$—O—$CFR^1R^2$ in which $R^1$ and $R^2$ are each H, in the liquid phase with a Lewis acid.

2. A process as claimed in claim 1 in which the Lewis acid comprises a fluoride of a metal.

3. A process as claimed in claim 2 in which the metal ion of the metal fluoride has a charge/radius ratio of at least 5.0.

4. A process as claimed in claim 3 in which the Lewis acid is selected from the fluorides of niobium, antimony, boron, titanium, tantalum, aluminium and tungsten.

5. A process as claimed in claim 3 which the metal fluoride is mixed with the α-fluoroether.

6. A process as claimed in claim 3 in which the metal fluoride is generated in situ from a metal and hydrogen fluoride.

7. A process as claimed in claim 1 which is carried out at a temperature in the range from about –b 30° C. to about 200° C.

8. A process as claimed in claim 1 wherein hydrogen fluoride is present and the ratio of hydrogen fluoride to said compound is in the range from about 1:2 to about 50:1.

\* \* \* \* \*